United States Patent
Kadziauskas et al.

(10) Patent No.: US 6,852,092 B2
(45) Date of Patent: Feb. 8, 2005

(54) HANDPIECE SYSTEM FOR MULTIPLE PHACOEMULSIFICATION TECHNIQUES

(75) Inventors: Kenneth E. Kadziauskas, Coto de Caza, CA (US); Mark E. Steen, Chino Hills, CA (US); Jimmie B. Allred, III, Skaneateles, NY (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 10/263,091

(22) Filed: Oct. 2, 2002

(65) Prior Publication Data

US 2004/0068270 A1 Apr. 8, 2004

(51) Int. Cl.[7] .......................... A61N 1/30; A61B 17/20; A61B 17/32; A61M 1/00; A61F 9/00
(52) U.S. Cl. ..................... 604/22; 604/27; 604/19; 604/35; 606/169; 606/107
(58) Field of Search .................... 604/22–35, 264, 604/19, 272, 265, 294, 902, 500–523, 48, 291, 191, 169, 410; 606/169, 107, 170, 171

(56) References Cited

U.S. PATENT DOCUMENTS

| | | |
|---|---|---|
| 3,805,787 A | 4/1974 | Banko |
| 4,032,803 A | 6/1977 | Durr et al. |
| 4,804,364 A | 2/1989 | Dieras et al. |
| 4,900,300 A | 2/1990 | Lee |
| 4,908,015 A | 3/1990 | Anis |
| 4,909,249 A | 3/1990 | Akkas et al. |
| 5,038,756 A | 8/1991 | Kepley |
| 5,059,204 A | 10/1991 | Lawson et al. |
| 5,084,012 A | 1/1992 | Kelman |
| 5,154,696 A | 10/1992 | Shearing |
| 5,217,465 A | 6/1993 | Steppe |
| 5,242,385 A | 9/1993 | Strukel |
| 5,413,556 A | 5/1995 | Whittingham |
| 5,486,162 A | 1/1996 | Brumbach |
| 5,562,610 A | 10/1996 | Brumbach |
| 5,562,612 A | 10/1996 | Fox |
| 5,634,912 A | 6/1997 | Injev |
| 5,718,676 A * | 2/1998 | Barrett ..................... 604/22 |
| 5,843,109 A | 12/1998 | Mehta et al. |
| 5,989,209 A * | 11/1999 | Barrett ..................... 604/22 |
| 6,254,587 B1 * | 7/2001 | Christ et al. ............. 604/521 |

* cited by examiner

Primary Examiner—Michael J. Hayes
Assistant Examiner—Roz Maiorino
(74) Attorney, Agent, or Firm—Peter J. Gluck; David C. Weber

(57) ABSTRACT

A handpiece system for multiple phacoemulsification procedures is provided which includes a housing having a distal end adapted for sealably and releasably engaging a plurality of nose cones and a sonic generator disposed within the housing. A horn having a body connected to the sonic generator and a needle is provided for radiating sonic energy into an eye for fragmenting eye tissue. A plurality of nose cones are provided which are adapted for being sealably and releasably engaged with the housing and provide structure enabling varied phacoemulsification procedures.

12 Claims, 1 Drawing Sheet

HANDPIECE SYSTEM FOR MULTIPLE PHACOEMULSIFICATION TECHNIQUES

Present invention generally relates to phacoemulsification procedures for removing cataractous lens tissue from a human eye and is more particularly directed to a handpiece system for conducting different phacoemulsification techniques utilizing different handpiece configurations.

A natural crystalline lens may become opaque or cloudy and this condition is commonly referred to as a cataract, or cataractous lens, which inhibits the clear transmission and focusing of light.

Techniques have been developed to surgically remove the cataract lens and replace it with an artificial, or interocular lens. The cataract lens extraction process may be performed by a number of medically recognized techniques. In early procedures, lens removal was effected through manual extraction which required a wound of about 12 mm in length. This large opening can result in corneal or scleral tissue damage.

Phacoemulsification enables the removal of cataractic lens through much smaller incision, for example, between at least about 2.2 to about 4 mm.

In one common phacoemulsification procedure, a needle is inserted through an incision into a lens capsule and a needle is sonically vibrated to mechanically emulsify the lens. Once fragmented, or emulsified, the lens material is aspirated through a lumen through the phacoemulsification needle.

While emulsifying the lens and aspirating lens fragments, a simultaneous flow of irrigation fluid is introduced into the lens capsule around the phaco needle through an annulus established by sleeve concentrically disposed over the needle.

The irrigation fluid is also necessary to prevent collapse of the interior chamber of the eye during-aspiration.

Other phacoemulsification procedures include the use of a vibrated needle without the use of a sleeve for introducing irrigation fluid. This enables even smaller incisions since an annulus for the flow of irrigation fluid is not required. In this procedure, a second needle is utilized for introducing the irrigation fluid into the eye. This procedure is described in U.S. patent application Ser. No. 09/894,503 entitled "Bi-Manual Phaco Needle" and is incorporated herewith by this specific reference theretofore for providing a description of a phacoemulsification procedures which can be implemented by the handpiece system in accordance with the present invention.

The present invention is directed to a handpiece system for multiple phacoemulsification procedures utilizing both concentric aspiration and irrigation fluid paths and a separate aspiration and irrigation fluid paths.

SUMMARY OF THE INVENTION

A handpiece system in accordance with the present invention for multiple phacoemulsification procedures generally includes a housing having a distal end adapted for sealably and releasably engaging a plurality of at least two interchangeable different nose cones. A sonic generator is disposed within a housing and a horn having a body, is connected to the generator, and a needle provided for radiating sonic energy into an eye for fragmenting eye tissue. The horn includes a lumen passing through the needle and body for aspirating fluid and fragmented eye tissue.

A first nose cone is provided and adapted for sealably and releasably engaging a housing distal end and having a sleeve for covering the needle. In addition, a second different interchangeable nose cone is provided and adapted for sealably and releasably engaging the housing distal end for establishing an annulus around the needle.

The second nose cone includes an inlet for receiving irrigation fluid and enabling irrigation fluid to pass over the needle and into the eye. Accordingly, the system in accordance with the present invention thus provides for a plurality of nose cones for enabling the handpiece system to perform a plurality of phacoemulsification procedures.

Multiple first and second nose cones may be provided and may be disposable or configured for sterilization separate from the handpiece.

The second nose cone includes a sleeve for the establishment of the annulus and a forward portion substantially smaller in diameter than a diameter of a housing diameter. This provides for a streamline shape for minimizing the visual field of a physician utilizing the handpiece.

The second nose cone inlet is positioned for introducing the irrigation fluid into the forward portion of the sleeve. Thus, the handpiece itself need not be configured with conduits, and the like, for the channeling or movement of irrigation fluid into the annulus. This configuration further reduces the diameter of the handpiece, which should be as small as possible in order to minimize any interference with the physicians' field of vision as well as reducing size and weight of the handpiece.

A tube is provided and disposed exterior to the housing for introducing irrigation fluid into the inlet. This structure enables an irrigation system which is completely separate and detachable from the handpiece housing.

The present invention further includes a nose cone for a handpiece system having a sonic generator, a horn having a body connected to the sonic generator, a needle for radiating a sonic energy into an eye for fragmenting eye tissue, the needle including a lumen, passing through the needle and body, for aspiration of fluid and fragmented eye tissue, and a housing for containing the sonic generator and horn, having a distal end and no conduits therein for the transport of fluid therethrough. In this embodiment the nose cone includes a fitting for sealably and releasably engaging the housing distal end along with a sleeve for covering the needle and establishing an annulus therearound. An inlet is provided for receiving irrigation fluid and enabling the irrigation fluid to pass through the annulus over the needle and into the eye.

More particularly the nose cone may include a forward portion substantially smaller in diameter than a diameter of a housing diameter and the nose cone inlet is positioned for introducing irrigation fluid into the forward portion. A tube may be provided and disposed exterior to the housing for introducing irrigation fluid into the inlet.

BRIEF DESCRIPTION OF THE DRAWINGS

The advantages and features of the present invention will be better understood by the following description when considered in conjunction with the accompanying drawings in which.

DETAILED DESCRIPTION

Figure 1:
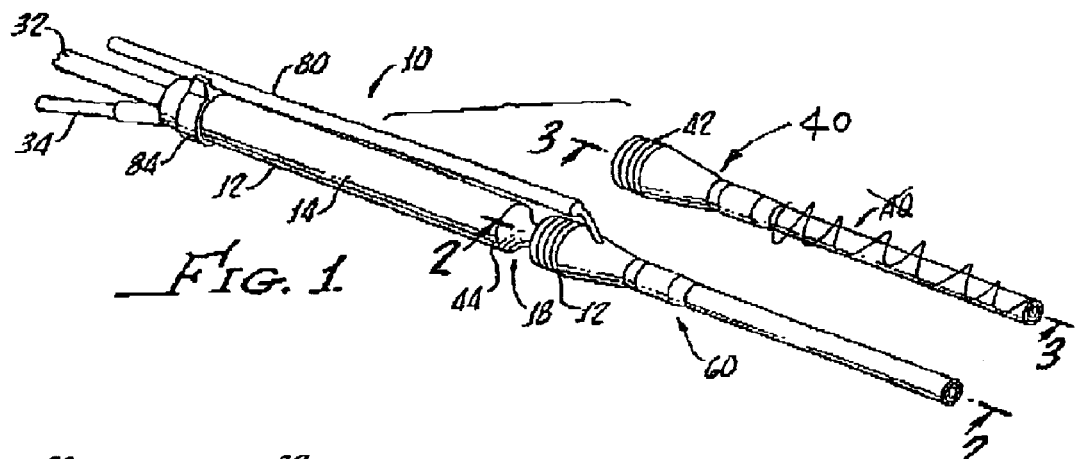
FIG. 1 is a perspective view of the handpiece system in accordance with the present invention generally showing a housing along with the first and second removable and exchangeable nose cones.

With reference to FIG. 1 there is shown a handpiece system 10 in accordance with the present invention for phacoemulsification procedures generally includes a housing 12 with a sonic generator 14 disposed therein. The sonic generator 14 may be of any suitable type, as for example, described in U.S. Pat. No. 5,843,109. This patent is incorporated herewith in its entirety by this specific reference thereto for teaching sonic generation in handpieces suitable for phacoemulsification procedures.

Figure 2:
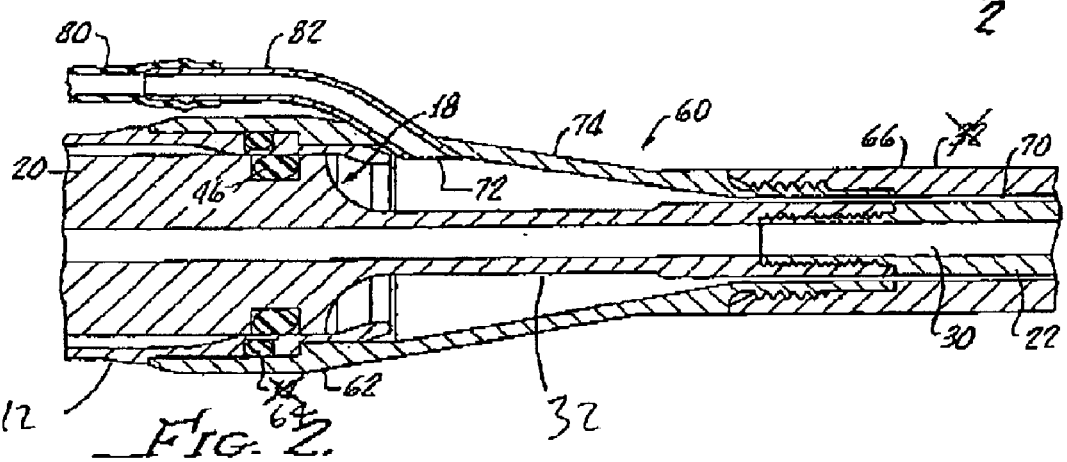
FIG. 2 is a cross sectional view taken along the line 2—2 of FIG. 1 showing a cross section of one of the plurality of nose cones in accordance with the present invention.
Figure 3:
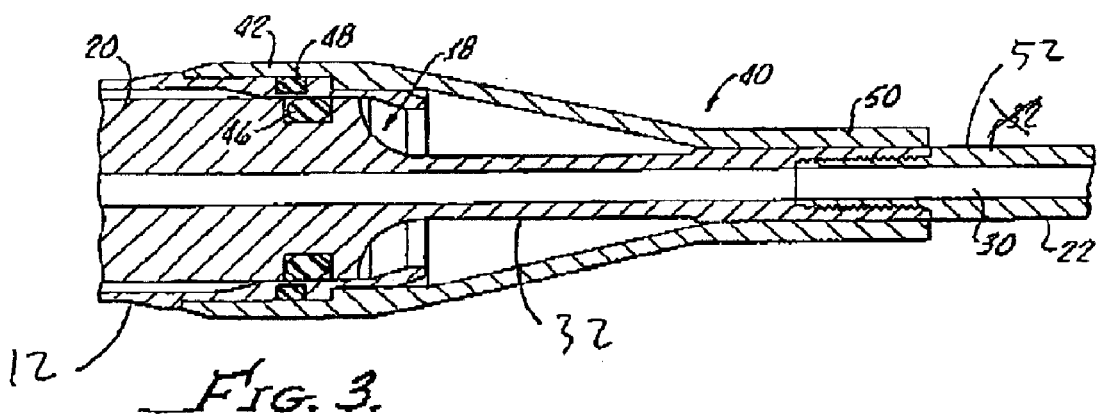
FIG. 3 is a cross sectional view taken along the line 3—3 of FIG. 1 showing a cross section of another of the plurality of nose cones in accordance with the present invention.

A horn 18 having a body 20 and a needle 22 is provided for radiating sonic energy into an eye (not shown), see FIGS. 2 and 3. The horn 20 and needle 22 includes a lumen 30 passing therethrough for aspiration of fluid and fragmented eye tissue(not shown). The horn 18 and body 20 are made of conventional materials suitable for use in phacoemulsification handpieces.

A lumen 30 communicates with an aspiration tube 32 exiting the housing 12 which is innerconnected with a suitable vacuum pump (not shown). In an electrical connection 34 provides power to the sonic generator 14 in a conventional manner.

With reference to FIGS. 1 and 3, the system 10 includes at least one first nose cone 40 which is adapted by way of a flange 42 for engaging a distal end 44 of the housing 12. A seal 46 disposed proximate the housing distal end 44 and a seal 48 disposed in the flange 42 provide for sealably and releasably engaging the first nose cone 40 with the housing distal end 44. The seals 46, 48 may be conventional in nature, such as, for example o-rings.

Other innerconnecting relationships may be provided between the nose cone 40 and the housing distal end 44, such as, conventional snap and lock, screw, or bayonet types of innerconnections all of which may be provided for sealably and releasably engaging the nose cone 40 with the housing 12 by way of the distal end 44. The nose cone 40 includes a sleeve portion 50 covering the needle 22 and exposing a portion 52 thereof extending beyond the sleeve 50.

The first nose cone 40 used in combination with the housing 12 provides for performing phacoemulsification procedures in a bi-manual nature as hereinabove noted and described in U.S. patent application Ser. No. 09/894,503 filed Jun. 28, 2001 entitled "BI-MANUAL PHACO NEEDLE". This phacoemulsification procedure enables phacoemulsification of eye tissue (not shown) through narrow openings in a sclera (not shown) as hereinabove described.

Being separate and removably attachable to the housing distal end 44, the nose cone 40 may be constructed of materials for enabling sterilization thereof, or made of materials suitable for one use methodology.

With reference to FIGS. 1 and 2, a second different interchangeable nose cone 60 is provided in accordance with the present invention which is adapted by way of a flange 62 including a seal 64 for engaging the distal end 46 in a manner similar to that described in connection with the first nose cone 40.

The second nose cone, however, includes a sleeve 66 which is sized for establishing a annulus 70 surrounding a intermediate section 22 and an inlet 72 for receiving irrigation fluid and enabling the irrigation fluid to pass over the needle 22 and into the eye (not shown).

The nose cone 60 includes a forward portion 74 having a diameter substantially smaller than a diameter of the housing 12. As hereinabove noted, this provides a diminished presence in the field of vision of the physician during a phacoemulsification procedure.

The nose cone inlet 72 is positioned for introducing irrigation fluid into the forward portion 74 thus entirely bypassing the housing 12. This enables removal of the nose cone 60 from the housing 12 and further enables a smaller diameter housing 12 for minimizing the presence of the housing in the physician's field of vision.

Irrigation is provided to the inlet through a tube 80 fitted to an inlet fitting 82.

A clip 84 may be provided to align the tube 80 along the housing 82 to further streamline the assembly of the nose cone 60 and housing 12. When assembled, the nose cone 60 and housing 12 provide a phacoemulsification handpiece for phacoemulsification procedures in which irrigation fluid and aspiration are conducted at a single site within an eye capsule (not shown).

The nose cone 60 may be constructed of materials suitable for sterilization or, of materials suitable for disposal of the nose cone 60 after a single use.

Although there has been hereinabove described a specific detachable nose piece for phacoemulsification handpiece in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A handpiece system for multiple phacoemulsification techniques, said handpiece system comprising:
   a housing having a distal end adapted for scalably and releasably engaging a plurality of at least two different interchangeable nose cones;
   a sonic generator disposed within said housing;
   a horn having a body connected to said sonic generator and a needle for radiating sonic energy into an eye for fragmenting eye tissue, said horn including a lumen, passing through the needle and body, for aspiration of fluid and fragmented eye tissue;
   a first interchangeable nose cone sealably and releasably engaging the housing distal end and configured to perform a bimanual phacoemulsification procedure in which irrigation fluid does not pass over the needle and into the eye; and
   a second different interchangeable nose cone sealably and releasably engaging the housing distal end for establishing an annulus surrounding said needle, said second nose cone including an inlet for receiving irrigation fluid and enabling the irrigation fluid to pass over said needle and into the eye.

2. The system according to claim 1 wherein said second nose cone comprises a sleeve for establishing the annulus and a forward portion substantially smaller in diameter than a diameter of a housing diameter.

3. The system according to claim 2 wherein the second nose inlet is positioned for introducing the irrigation fluid into the forward position.

4. The system according to claim 3 further comprising a tube, disposed exterior to said housing, for introducing irrigation fluid to said inlet.

5. The system according to claim 1 further comprising a plurality of first nose cones and a plurality of second nose cones, all of the nose cones being disposable.

6. A handpiece system for multiple phacoemulsification techniques, said handpiece system comprising:

a housing having a distal cad;

a sonic generator disposed within said housing;

a horn having a body connected to said sonic generator and a needle for radiating sonic energy into an eye for fragmenting eye tissue, said horn including a lumen, passing through the needle and body, for aspiration of fluid and fragmented eye tissue;

a plurality of at least two different interchangeable nose cones for enabling the handpiece system to perform a plurality of phacoemulsification procedures, each of the nose cones being adapted for sealably and releasably engaging the housing distal end and including:

a first interchangeable nose cone configured to perform a bimanual phacoemulsification procedure in which irrigation fluid does not pass over the needle and into the eye: and a second different interchangable nose cone configured to perform a phacoemulsification procedure in which irrigation fluid may pass over the needle and into the eye.

7. The system according to claim 6 wherein one of said plurality of nose cones includes a sleeve for establishing an annulus around said needle.

8. The system according to claim 7 wherein one of said plurality of nose cones includes an inlet for receiving irrigation fluid and enabling the irrigation fluid to pass through the annulus and into the eye.

9. The system according to claim 8 wherein one of said plurality of nose cones includes a forward portion substantially smaller in diameter than a diameter of a housing diameter.

10. The system according to chum 9 wherein the inlet is positioned for introducing the irrigation fluid into the forward position.

11. The system according to claim 10 further comprising a tube, disposed exterior to said housing, for introducing irrigation fluid to said inlet.

12. The system according to claim 6 wherein each of said plurality of nose cones are disposable.

\* \* \* \* \*